US005894092A

United States Patent [19]
Lindgren et al.

[11] Patent Number: 5,894,092
[45] Date of Patent: Apr. 13, 1999

[54] METHOD AND SYSTEM FOR OBTAINING NEAR-SURFACE CHARACTERISTICS OF MATERIALS USING ULTRASONIC RAYLEIGH WAVES

[75] Inventors: Eric A. Lindgren, Gaithersburg; Moshe Rosen, Rockville; Harold Berger, Gaithersburg, all of Md.

[73] Assignee: Industrial Quality, Inc., Gaithersburg, Md.

[21] Appl. No.: 09/003,124

[22] Filed: Jan. 6, 1998

Related U.S. Application Data

[63] Continuation-in-part of application No. 08/722,795, Sep. 27, 1996, Pat. No. 5,767,408.
[51] Int. Cl.$^6$ ............................................. G01N 29/08
[52] U.S. Cl. ............................................. 73/598
[58] Field of Search ........................ 73/597, 598, 599, 73/600, 602, 624, 625, 627, 628; 310/313 R, 336

[56] References Cited

U.S. PATENT DOCUMENTS

| 4,009,104 | 2/1977 | Behrendt et al. ............. 210/744 |
|---|---|---|
| 4,038,865 | 8/1977 | Flambard et al. ............. 73/628 |
| 4,274,288 | 6/1981 | Tittmann et al. ............. 73/602 |
| 4,313,070 | 1/1982 | Fisher ............. 73/627 |
| 4,372,163 | 2/1983 | Tittmann et al. ............. 73/602 |
| 4,462,256 | 7/1984 | Moffett ............. 73/642 |
| 4,503,708 | 3/1985 | Kino et al. ............. 73/628 |
| 4,765,750 | 8/1988 | Wadley ............. 374/137 |
| 4,854,173 | 8/1989 | Mott et al. ............. 73/600 |
| 5,035,144 | 7/1991 | Aussel ............. 73/602 |
| 5,763,786 | 6/1998 | Camplin et al. ............. 73/643 |
| 5,767,408 | 6/1998 | Lindgren et al. ............. 73/597 |

OTHER PUBLICATIONS

Eric A. Lindgren, Thomas S. Jones, Harold Berger, and M. Rosen, "Determining Residual Stress in Plates with Rayleigh Waves", ASNT Spring Conference Summaries, Mar. 1995, pp. 52–54.

Eric A. Lindgren, Thomas S. Jones, Harold Berger and M. Rosen, "Determining Residual Stress in Plates With Rayleigh Waves", Aug. 1993, pp. 1–8.

Technical Information Services American Institute of Aeronautics and Astronautics, "Stress Measurement By Ultrasonic Techniques", Oct. 1973, pp. 1–30.

B.G.Martin, "The Measurement of Surface and Near–Surface Stress in Aluminum Alloys Using Ultrasonic Rayleigh Waves", Feb. 1974, pp. 229–234.

*Primary Examiner*—Hezron Williams
*Assistant Examiner*—Rose M. Miller
*Attorney, Agent, or Firm*—Burns, Doane, Swecker & Mathis, L.L.P.

[57] ABSTRACT

In a method for obtaining near-surface characteristics of a material, a series of single frequency ultrasonic Rayleigh waves are generated, with a generating system, in the material. The Rayleigh waves are detected with a detection system remote from the generating system. Velocities of the detected Rayleigh waves are determined at the selected frequencies. A depth profile of one or more characteristics of the material is prepared based on the determined Rayleigh wave velocities.

12 Claims, 3 Drawing Sheets

METHOD AND SYSTEM FOR OBTAINING NEAR-SURFACE CHARACTERISTICS OF MATERIALS USING ULTRASONIC RAYLEIGH WAVES

The present application is a continuation-in-part of U.S. patent application Ser. No. 08/722,795, filed Sep. 27, 1996, now U.S. Pat. No. 5,767,408.

FIELD OF THE INVENTION

The present invention relates to methods and systems for obtaining near-surface characteristics of materials using ultrasonic Rayleigh waves and, more particularly, to such methods and systems wherein changes in material characteristics at different depths of the material are determined as a function of changes in wave velocity for different wave frequencies.

BACKGROUND AND SUMMARY

Ultrasonic methods are well established in the field of nondestructive material evaluation. Most previous methods are based on bulk ultrasonic waves. Bulk ultrasonic waves, called longitudinal and shear waves, may be used for materials characterization and flaw detection. Longitudinal waves have a particle displacement which is parallel to the direction of propagation. For shear waves, the particle displacement is perpendicular to the direction of propagation. The frequency of these waves is above the audible range. Therefore, they are labeled as ultrasonic waves. For nondestructive evaluation, the ultrasound is in the form of stress waves having amplitudes that are sufficiently small to remain in the elastic regime and not cause any permanent deformation of the material in which the ultrasonic waves are propagating.

The velocities of the bulk ultrasonic waves are well known to be dependent on the elastic properties of the material. The velocity of an ultrasonic wave is determined by the interatomic forces that bond the material together. Thus, the velocity of an ultrasonic wave is directly dependent on the mechanical properties of the material. If there is a change in the mechanical properties, it is detected as a change in the velocity. Therefore, chemical and compositional changes in the material may be detected as changes in the ultrasonic velocity.

Bulk ultrasonic waves are merely one mode of propagation. As indicated by their name, they require a bulk material in which to propagate. The theoretical work that has been performed with these materials typically applies to semi-infinite half-spaces that do not have any geometrical constraints. Another class of ultrasonic waves is surface waves. Ultrasonic surface waves, or so-called "Rayleigh waves," are bound to the surface of the material in which they propagate. They have several unique physical parameters that are used in the present invention for determining the depth profile of material properties. These features include a non-dispersive nature, a penetration depth into the material of approximately one wavelength, and the ability of control of penetration depth by altering wavelength.

When an ultrasonic wave is non-dispersive, its velocity is independent of its frequency. Thus, the velocity of the Rayleigh wave does not change when the frequency of the wave is altered. Using the well known equation in ultrasonics that the velocity is equal to the wavelength multiplied by the frequency, it is clear that if the frequency of a non-dispersive wave changes, the wavelength must also change to maintain the constant velocity. Thus, as the frequency of a Rayleigh wave decreases, the wavelength must increase.

When the wavelength increases, the penetration depth of the Rayleigh wave must also increase. Typically, the penetration depth of a Rayleigh wave in a material is said to be about one wavelength. However, the exact penetration depth is dependent on the properties of the material and may vary between about 1.15 and 1.25 wavelengths in depth. The exact amount of energy that is carried in the final 20 percent of the penetration depth is typically not accounted for as it contains a very small percentage of the overall energy of the Rayleigh wave. The amplitude of the wave decreases by an exponential function, resulting in very little energy in the final penetration depth beyond one wavelength.

The prior art has made use of certain of these unique features of Rayleigh waves to simplify the development of nondestructive materials evaluation methods. As expected, most of these efforts have concentrated on the use of Rayleigh waves to determine near-surface phenomena. It is, for example, known to use the frequency dependent penetration depth characteristics of Rayleigh waves to determine the depth of surface breaking cracks. U.S. Pat. No. 4,274,288 to Tittmann et al. discloses a method for determining the depth of a surface flaw based on generating a Rayleigh surface wave that interacts with the flaw. A sensor is used to determine the acoustic signal reflected from the flaw, which includes one portion of the signal from the surface edge of the flaw and a second portion of the signal from the bottom of the flaw. The depth of the flaw is determined from analyzing the interference between the two portions of the reflected signals in the frequency domain. The signals are converted to the frequency domain by means of a Fourier transform. The crack depth is determined by selecting the frequency for the maximum amplitude of the frequency domain response, which is independent of the angle of detection, and converting this frequency into a crack depth using a formula given in the patent.

U.S. Pat. No. 4,372,163 to Tittmann et al. discloses the use of broadband generation and detection of Rayleigh waves for materials evaluation. The signals are detected at two locations along the travel path of the Rayleigh wave. The signals are converted into the frequency domain using a Fourier transform. The dispersion of the wave in the surface is calculated by utilizing the distance between the first and second locations and the change in phase of the frequency components of the detected waves between the first and second locations. The calculated dispersion data is inverted to derive a subsurface profile of the physical structure of the object to characterize the surface properties of the object.

U.S. Pat. No. 4,765,750 to Wadley discloses the use of narrow band electromagnetic acoustic transducers to obtain Rayleigh wave velocities at several distinct frequencies. Once the velocities are obtained at each frequency, the results are plotted to determine the velocity changes as a function of frequency. The velocity changes indicate the presence of changes in the material properties at different depths. By performing these measurements, the depth profile of the material properties can be obtained. By this method, changes in temperature as a function of depth may be measured after the material has been cast.

According to one aspect of the present invention, a method for obtaining near-surface characteristics of a material is disclosed. According to the method, a broadband ultrasonic Rayleigh wave including a plurality of components is generated, with a generating system, in the material. The Rayleigh wave is detected with a detection system remote from the generating station. The detected Rayleigh wave is filtered to obtain selected ones of the plurality of components of the detected Rayleigh wave at selected frequencies. Velocities of the selected components of the detected Rayleigh wave are determined at the selected frequencies.

According to another aspect of the present invention, a system for determining near-surface characteristics of a material includes a generator for generating a broadband ultrasonic Rayleigh wave having a plurality of components in the material. The system further includes a detection system for detecting the Rayleigh waves. A filter arrangement is provided for filtering the detected Rayleigh waves to obtain selected ones of the plurality components of the detected Rayleigh waves at selected frequencies, and a processor is provided for determining velocities of the selected components of the detected Rayleigh wave at the selected frequencies.

According to another aspect of the present invention, a method for obtaining near-surface characteristics of a material is disclosed. According to the method, a series of single frequency ultrasonic Rayleigh waves are generated, with a generating system, to provide a plurality of Rayleigh waves in the material. The Rayleigh waves are detected with a detection system remote from the generating station. Velocities of the detected Rayleigh waves at the frequency generated by the generating equipment are determined. A depth profile of one or more characteristics of the material is prepared based on the determined Rayleigh wave velocities.

According to yet another aspect of the present invention, a system for determining near-surface characteristics of a material is disclosed. The system includes a generator for generating a series of single frequency ultrasonic Rayleigh waves in the material. The system also includes a detection system, remote from the generator, for detecting the Rayleigh waves at the frequency generated by the generator. The system also includes processing means for calculating Rayleigh wave velocities based on a time of flight from generation of the Rayleigh waves by the generator to detection of the Rayleigh waves by the detection system and for preparing a depth profile of one or more characteristics of the material based on Rayleigh wave velocities.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
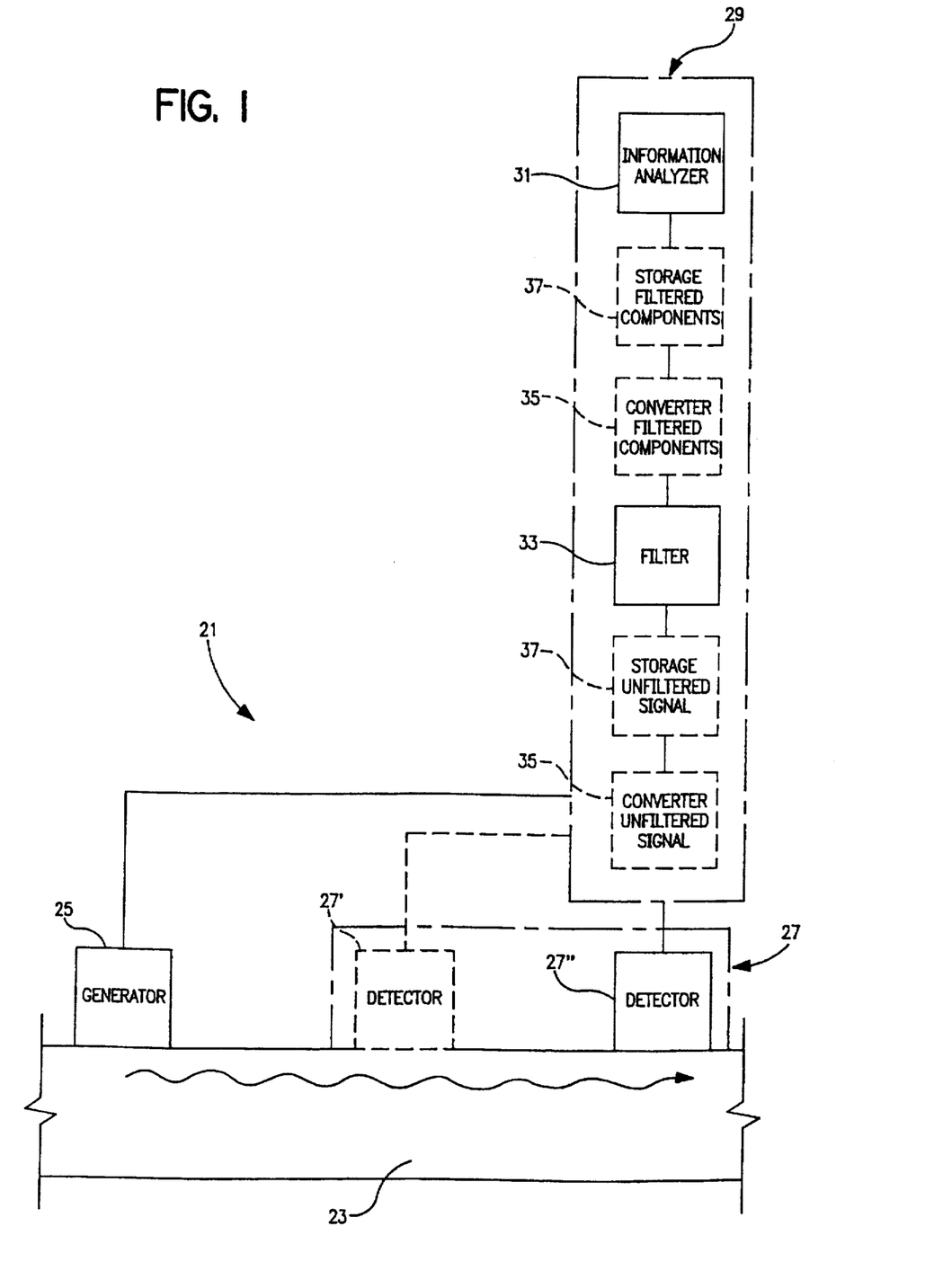
FIG. 1 schematically shows a system according to an embodiment of the present invention.

A system 21 according to an embodiment of the present invention is shown schematically in FIG. 1. The system 21 uses non-dispersive ultrasonic Rayleigh surface waves, which have a penetration depth of about one wavelength, to map the depth profile of the near-surface property changes and other near-surface phenomena in a material 23. From the relationship between frequency, wavelength, wave penetration, and velocity, measurement of the velocity of waves or wave components at different frequencies corresponds to measurement of the velocity of those waves or wave components at particular depths in the material 23. Thus, if there are differences in the properties of the material 23 at different depths in the material, they are detected by observing changes in the velocity of the Rayleigh wave or components thereof at different frequencies.

The system 21 comprises a combination including equipment 25 for the generation of ultrasonic Rayleigh waves in the material 23 at different frequencies, equipment 27 for the detection of ultrasonic Rayleigh waves in the material 23 at different frequencies, and processing equipment 29 including analysis equipment 31 for determining the velocity of the Rayleigh waves at the different frequencies. The processing equipment 29 and the analysis equipment 31 may comprise equipment such as dedicated electronic equipment or computer equipment. A significant advantage of the system 21 lies in its versatility, in that it may be adapted for use with a broad range of Rayleigh wave generation and detection equipment. The generation and detection equipment includes various known types of piezoelectric transducers and electromagnetic transducers, as well as other types of equipment. The processing and analysis of signals from the generation and detection equipment to obtain velocity measurements can be performed electronically on the basis of analog signals, or through computer analysis of digitized signals.

According to a preferred embodiment of the present invention, a system for determining near-surface characteristics of a material includes a generator for generating a series of single value ultrasonic frequencies, known as tone bursts, thereby generating in the material a plurality of ultrasonic waves. The tone burst method for generating the ultrasonic Rayleigh wave is based on using an electrical burst of, preferably, five or more cycles of a sinusoidal wave tuned to a singular frequency. The use of the tone burst approach simplifies the detection process in that no filters are required. The equipment is otherwise the same as that shown in FIG. 1. Each selected ultrasonic frequency is detected and analyzed to determine velocities of the detected Rayleigh waves. With the tone burst approach, it is possible to use one broadband transducer and multiple tone bursts of different resonant frequencies to obtain Rayleigh waves with different frequencies. With different frequency Rayleigh waves, the desired depth profile of the material property variations can be obtained without changing the generating or detecting profiles, which is an important advantage for field inspections of material.

According to another embodiment of the invention, near-surface properties of the material 23 are determined through the use of a single measurement with broadband ultrasonic Rayleigh surface waves. The detected Rayleigh wave is preferably processed by a bandpass filter 33, either in analog or digital form, followed by an automated determination of the velocity for each filtered component of the Rayleigh wave. With the velocity values for the penetration depths determined by the frequency range of the bandpass filter, the depth profile of the material can be established. If a reference measurement is required to determine the Rayleigh wave velocity of the material that has been subjected to a near-surface process, this measurement can be obtained by performing a Rayleigh wave measurement at a very low frequency to achieve a penetration depth much greater than the region subjected to the near-surface process.

The filter 33 is preferably in the form of analog filters applied directly to the detected Rayleigh wave, or computer based filters applied to a digitized Rayleigh wave. The processor 29 determines the velocities at the different frequency values either in analog format, in digital format after analog filtering, or in digital format after digital filtering. It will be recognized that the level of sophistication of the system 21 may be user selected to best fit the user's specific inspection/process control application.

The Rayleigh wave detected by the detecting system 27 is filtered by the filter 33 in a manner similar to the filtering of an electrical wave by a bandpass filter. Analog filters, such as the bandpass filters manufactured by Microwave Filter Company, East Syracuse, N.Y., or Mini-Circuits, Brooklyn, N.Y., may be provided that operate in the ultrasonic frequency range, which ranges from 0.05 to 100 MHz. Such filters are selected for the appropriate bandpass that matches the wave frequencies required for the penetration depths that are of interest in the specific application. Analog filters are presently believed to be of primary interest in those applications that are more repetitive for a set value of penetration depths. If multiple bandpasses are required, the broadband signal can be split into different filters and the resultant signal analyzed for each bandpass value.

The broadband signal may also be digitized prior to filtering. Suitable digitizers for use in connection with the present invention include the LeCroy Model 9450A digital oscilloscope, made by LeCroy Corp., Chestnut Ridge, N.Y. Once the signal is in digital form, the signal can be stored and subsequently filtered with custom software filters to identify the changes of the surface wave velocity at specific penetration depths of interest. If a wide range of depths are investigated, it may be desirable to filter with multiple filters to obtain a more complete depth profile of the velocity changes as a function of penetration depth. The signal may be also be converted to digital format after analog filtering, and then be processed in digital format, either with or without storing of the signal, as desired or necessary. If it is desired or necessary to convert the Rayleigh wave signal to a digital signal, a converter 35 is provided before or after the filter 33, as desired or necessary.

Wave Generation Equipment

According to a particularly preferred embodiment of the invention, near-surface properties of the materials are determined through the use of a series of measurements with tone-burst generated ultrasonic Rayleigh waves. The detected signals can be immediately associated with the generated ultrasonic frequency and the ultrasonic velocity for each frequency. With the velocity values for the penetration depths determined by the generated frequency of the tone burst, the depth profile of the material can be established, including case depth, coating thickness, chemical variations in the material, and the like.

According to one embodiment of the present invention, Rayleigh wave generation equipment 25 preferably includes a well known piezoelectric transducer and a mode conversion wedge or block arrangement. With this generating equipment 25, the bulk ultrasonic wave that is generated by the transducer propagates through the mode conversion wedge at a specific angle, called the critical angle, which causes the energy of the bulk wave to be converted into a Rayleigh wave. The mechanism for this process is a result of boundary conditions and the angle of the ultrasonic wave. The angle can be determined by Snell's Law. To generate the bulk ultrasonic wave in the mode conversion wedge, an electrical impulse is used to stimulate the piezoelectric transducer. This pulse can be a spike pulse to cause the piezoelectric to resonate at its fundamental resonant frequency, or it can be a tuned radio frequency pulse to drive the piezoelectric at a frequency different from its fundamental resonant frequency. When the piezoelectric is driven at a frequency different from its fundamental resonant frequency, it is preferred to drive the transducer at a multiple of its fundamental frequency to avoid reductions in the efficiency of the generation process.

According to another embodiment, where the material 23 is an electrically conductive material, the Rayleigh wave generating equipment 25 may include an electromagnet acoustic transducer (EMAT). An EMAT suitable for use in connection with the present invention is available from Ultrasonics, Inc., San Luis Obispo, Calif. Oscillatory forces are generated within the skin depth of a conducting material when it is subjected to a static magnetic field and eddy currents induced by an electromagnetic wave. The oscillatory forces are the ultrasonic wave. The electromagnetic wave can be oriented so that the resulting oscillation causes Rayleigh waves to be generated. One advantage of the use of EMATs to generate Rayleigh waves is that EMATs do not require a liquid couplant between the transducer and the material. However, they do require contact between the sample and the transducer in order to efficiently transfer the electromagnetic wave. EMATs are very sensitive to lift-off factors which can alter the ultrasonic signal. In addition to the foregoing, other known approaches and equipment for generating Rayleigh waves, such as laser generation may be used. In laser generation, a pulse of laser light interacts with the surface of the material to cause a thermoelastic response or an ablative response. In the thermoelastic regime, the laser pulse causes localized heating of the sample surface, resulting in a rapid and localized thermal expansion of the material. The result of this thermal shock, amongst others, is Rayleigh waves. In the ablative regime, the laser light is typically focused into a point source, increasing the energy density that is striking the material. This causes localized vaporization of the near surface material, ablating it from the surface of the material. The shock to the material is caused by this ablation process. Rayleigh waves are generated by this process, but are typically lower in energy than those generated by thermoelastic means. The equipment required for laser generation include the laser and the necessary optical lens and mirrors to direct and, if implemented, focus the laser light. Appropriate lasers for this application are typically infrared Nd:YAG lasers, although others, such as argon and helium-neon, have been used. A source for low powered pulsed Nd:YAG lasers is Kigre Lasers, Hilton Head, N.C., and for high powered pulsed Nd:YAG lasers is Continuum, Santa Clara, Calif. A source for optical components is Newport Corporation, Irvine, Calif.

Known Rayleigh wave generation techniques permit obtaining a broadband signal that encompasses many frequencies. For example, a laser generated Rayleigh wave typically contains a frequency range of over 5 MHz. Also, it is possible to control the frequency content of the laser generated signal by altering the size of the laser beam spot on the sample surface. Similar broadband signals can be obtained with piezoelectric and other generation and detection techniques using known methods. For example, Rayleigh wave transducers based on piezoelectric generation for providing a frequency range of 1.0 to 20 MHz are available from Krautkramer-Branson, Lewistown, Pa. Piezoelectric transducers, by their nature, do not have a broadband response, and several transducers are used to obtain the above-mentioned frequency range.

Wave Detection Equipment

Most preferred wave detection equipment 27 operates by reversing the operation of the wave generation equipment 25. For example, a Rayleigh wave that approaches a mode conversion wedge will convert into a bulk ultrasonic wave that will travel from the sample surface at the critical angle. This wave can then be detected with a standard piezoelectric receiver. The time-of-flight of the Rayleigh wave from leaving a mode conversion wedge of the wave generating equipment 25 to reaching a mode conversion wedge of the wave detecting equipment 27 can be determined by subtracting the time-of-flight in the mode conversion wedges. Any desired combination of generation and detection techniques can be used. For example, EMAT generation can occur with piezoelectric detection and vice versa.

There is a wide selection of piezoelectric detection systems as a result of the development of broadband piezoelectric receivers for the acoustic emission testing industry. These devices can detect signals with significantly greater bandwidths than current commercial piezoelectric transducers available for conventional ultrasonic testing. Also, it is possible to detect signals at harmonics of the fundamental resonant frequency of commercial piezoelectric transducers. Additional detection methods include laser based detection systems such as interferometers which detect the displacement, or the velocity of the displacement, of a material's surface as a Rayleigh wave moves through an area illuminated by a probe beam.

Processing Equipment

An embodiment of the processing equipment 29 is described, for purposes of this application, as comprising the filter 33 and the analysis equipment 31. If desired or necessary, the processing equipment 29 may also include digital conversion equipment 35 for converting the filtered or unfiltered Rayleigh wave into digital information, and storage equipment 37, such as computer memory, for storing the digital information. The analysis equipment 31 preferably performs the analysis either by electronic analysis, such as with dedicated electronic equipment, or by computer analysis of digitized ultrasonic signals. Computerized analysis is presently preferred because it is believed to offer greater versatility, particularly in that the parameters of the analysis may be readily altered depending on a particular material inspection scenario. Therefore, advantages of the computerized approach include the ability to select and modify the desired frequency windows used to analyze the received Rayleigh waves, store the data, perform post measurement analysis, and archive the information for documentation. However, an advantage of the electronic approach is the increase in speed at which the measurements can be performed, especially if many units are required for a dedicated inspection process. As noted, however, the tone burst approach eliminates the need for a filter, and it will be appreciated that the filter is preferably omitted from the description of the invention as it applies to the tone burst approach.

The analysis equipment 31 determines the time-of-flight of the ultrasonic signal over a known distance in the material 23. If the ultrasonic signal is digitized, the time-of-flight can be determined by an amplitude gate with a specific cut-off level. The received Rayleigh wave will exceed the amplitude level and the arrival of the Rayleigh wave is recorded. The time-of-flight is determined by the analysis equipment 31 by subtracting the start time for when the wave was generated by the generating equipment 25 from the arrival time for when the wave was received by the detecting equipment 27. The Rayleigh wave velocity is determined by dividing the known distance between the generating equipment 25 and the detecting equipment 27 by the time-of-flight. Alternatively, the detection equipment may comprise two detection devices 27' and 27", separated by a known distance. The time-of-flight between the two detection devices can be obtained by using detection by the first detector 27' as a start signal and detection by the second detector 27" as an end signal for a timing system. The latter system is preferred if a high precision measurement is required. If the surface of the material 23 is not smooth, an optical profilometer can be used to determine the exact distance between the two locations on the sample where the time-of-flight measurement is made.

The processor 29 may process the filtered Rayleigh wave data in analog or digital format. For example, the processor may comprise an analog circuit that performs time-of-flight measurements of the Rayleigh wave signal detected by the detecting system 27 after the signal has been bandpass filtered by the filter 33. As such analog circuits are fixed once they have been manufactured, it is presently preferred to use such circuits in specific repetitive inspection applications. A preferred alternative is for the processor 29 to process the Rayleigh wave data after the signal has been digitized. Preferably, the digitized information is stored in a suitable storage device 37. The digitized information can be stored by the storage device 37 before or after filtering, as desired or necessary. After digitization of the information, the analysis equipment 31 performs all of the analyses, including time-of-flight determination, velocity calculation, and depth profile generation, using a dedicated software package. The frequency windows of the bandpass filters are preferably specified in the software for allowing custom depth profiles to be generated as required by the particular application for which the apparatus 21 is used.

When the tone-burst approach is used, because the Rayleigh waves are generated at a single frequency, the measurement process that characterizes the depth profile of the near surface material properties is preferably calibrated so that there is some reference velocity to compare the detected velocities to. There are several techniques by which this may be done. One approach is to retain a reference specimen of the material that is being examined. The calibration measurements on this sample can be compared to the results obtained from processed samples with the near surface property modifications or variations. Such surface modifications from processing may include those resulting from heat treatments, shot peening, ion implantation, and the like. As an alternative to the approach of retaining a reference specimen, because the ultrasonic measurement is non-destructive, the calibration measurements may be made on a sample prior to processing the sample, e.g., by heat treatments, shot peening, ion implantation, etc. Yet another alternative is to perform calibration measurements during the processing of the material. The results obtained from the calibration measurement made during processing can be used for process control, in addition to being used as calibration measurements.

Other calibration measurement approaches can be performed after processing of the material. According to one approach, the calibration measurement is performed in an area that is not affected by processing of the material. This approach is best suited in situations such as were a structure is welded and the calibration measurement is obtained in an area that is not affected by heating from the welding operation. Another approach is to eliminate the presence of the near-surface modifications resulting from processing, and then calibrate the sample. This approach is best suited for structures having unwanted residual stresses, where the magnitude and depth profile of the stress can be compared to a section of the material that is annealed to eliminate the stress field.

Operation of Method and Apparatus

As noted above, ultrasonic wave velocity in a material is directly dependent on the mechanical properties of the material, i.e., is constant for a material having particular mechanical properties; penetration depth of Rayleigh waves is generally considered to be about one wavelength; Rayleigh wave velocity is independent of frequency; and Rayleigh wave velocity is equal to wavelength times frequency. Thus, for a material having uniform mechanical properties, Rayleigh wave velocity is constant at all depths, and as frequency is decreased, wavelength and, relatedly, wave penetration depth increases. A profile of velocity of the Rayleigh wave as a function of depth can thus be determined by measuring wave velocity at different frequencies. From these measurements, the near-surface properties of the material 23 can be determined. For example, measured velocities deviating from expected velocities will indicate differences in material properties from the expected or desired. If desired, the system 21 may be provided with an alarm that alerts a user to deviations of measured velocities from expected or desired velocities that are indicative of problems with the material properties.

Advantages of the present invention have been demonstrated through Rayleigh wave velocity measurements at different frequencies to characterize near-surface phenomena, more particularly, lithium depletion in aluminum-lithium alloys. Lithium depletion can occur in this class of alloys when they are heat treated. The result is a thin layer of material in the near-surface area of this alloy that has less than a desired amount of lithium, resulting in inferior mechanical properties that affect the performance of the material. The heat treatments caused the lithium in the near-surface area to deplete from the sample, resulting in a band of material with different elastic properties than the bulk of the material. Lithium typically strengthens aluminum-lithium alloys by forming a coherent precipitate within the lattice structure of the alloy. Without the lithium present, the strengthening mechanism does not occur, resulting in a material with a lower elastic modulus. Currently, only surface measurement techniques are used to detect the area of lithium depletion. Such techniques cannot provide information concerning the depth of the lithium depletion.

Figure 2:
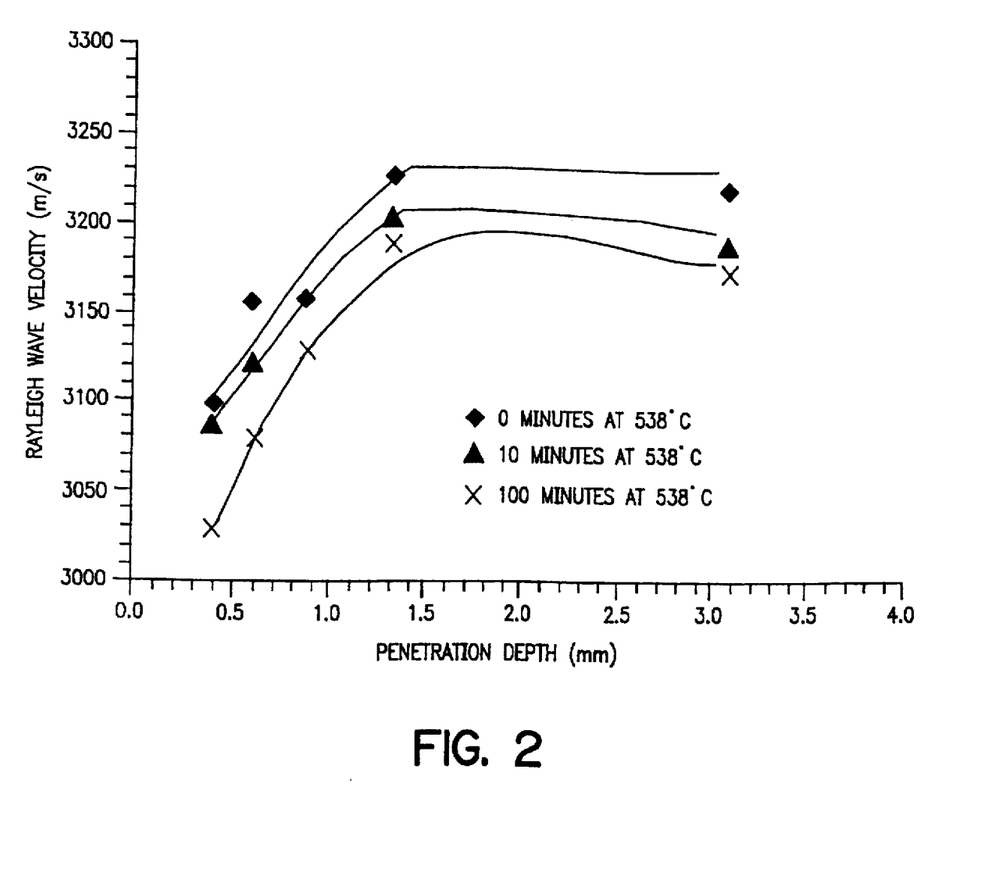
FIG. 2 is a graph of frequency velocity for several aluminum-lithium samples that have been heat treated to induce different levels of lithium depletion.

Several samples of aluminum-lithium alloy were deliberately heat treated to generate areas of lithium depletion. The samples were subsequently tested using Rayleigh waves generated at five different frequencies. A graph of the velocities for each frequency versus the penetration depth of the Rayleigh wave for that frequency is shown in FIG. 2. Since lithium depletion decreases the mechanical properties of the material, Rayleigh wave velocity decreases with increasing lithium depletion, i.e., decreasing or inferior mechanical properties. Also, in this example, Rayleigh wave velocity increases with increasing penetration depth, i.e., where lithium depletion is less severe or mechanical properties are superior as compared to at the more severely affected surface of the material. The graphs thus comprise a depth profile of changes in the lithium content in the alloy. Optical microscopy confirms the phenomena indicated by the depth profile prepared from the Rayleigh wave velocity measurements, and shows that lithium depletion increases in a gradual manner towards the surface of the sample. In FIG. 2, the sample with 100 minutes of additional heat treatment has the greatest amount of lithium depletion, the sample having 10 additional minutes has an intermediate amount of depletion, and the sample with 0 additional minutes has the least depletion. Normal heat treatment procedures for aluminum-lithium alloys induce lithium depletion in the near surface region. The above-mentioned samples thus have an initial amount of lithium depletion prior to the additional heat treatment.

Advantages of the present invention were further demonstrated where a broadband Rayleigh wave was filtered, and the depth profile was produced through a single measurement. Laser generation techniques were used to obtain a broadband Rayleigh wave. The frequency content of the Rayleigh wave was approximately 5.0 MHz. The Rayleigh wave was detected by a stabilized Michelson interferometer, which had a bandwidth greater than 5 MHz. The signal was digitized using a digital oscilloscope, from which the waveform was transferred to a desktop computer. A software package was used to construct two bandpass filters, one between 1.5 and 2.0 MHz, the other between 3.0 and 3.5 MHz. The received Rayleigh wave was filtered by the two bandpass filters. Comparison of the two filtered waveforms, as in FIG. 3, reveals a change in the time-of-flight between the two bandpass filtered signals. The magnitude of the difference was found to be equivalent to the difference determined from measurements performed using narrow band generators and detectors. Because the travel path and frequency ranges involved in the results illustrated in FIG. 3 result in arrival times of the waveforms being fairly small, i.e., on the order of 60 ns, the difference is difficult to resolve over a scale such as in the illustration, although different experimental scenarios can be arranged whereby the differences are more easily resolved visually. The location of the arrival time of an ultrasonic wave may be determined using a variety of electronic and/or digital methods. One technique is to use an amplitude threshold detector that notes when the amplitude of the received ultrasonic wave exceeds a preset value and records that specific time as the arrival time. This can be done electronically, but it is far more common to digitize the ultrasonic wave and perform this analysis by a computer software program. According to another technique, the threshold is set to detect the initial deviation from the baseline of the signal, denoting this initial deviation as the arrival of the ultrasonic signal. This method is typically accompanied by some signal processing, such as averaging, to minimize the noise level in the baseline signal.

Figure 3:
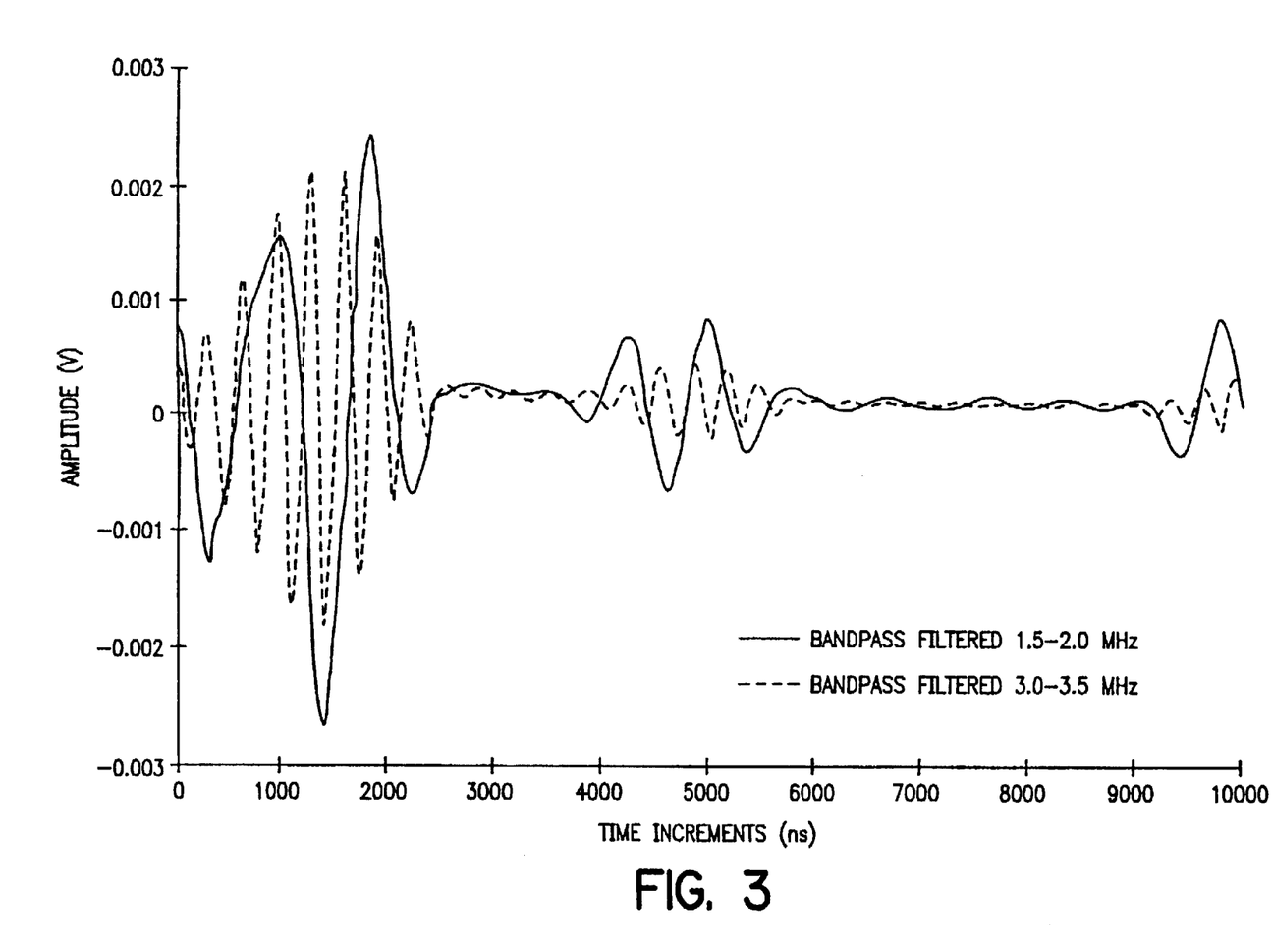
FIG. 3 is a graph comparing two filtered waveforms showing a change in the time-of-flight between the two bandpass filtered signals.

The resolution of the time difference between the waveforms after bandpass filtering can be enhanced by increasing the travel path between the generation and detection sites. Also, the resolution can be improved by decreasing the rise time of the bandpass filters.

The equipment and methodology described above is not limited to detecting changes in mechanical properties but, rather, is applicable to any phenomena that directly affect ultrasonic velocities. For example, the Rayleigh wave velocity measurements may also be used to measure residual stresses in materials as a function of depth. Residual stresses are a great concern in manufacturing as they often occur in welding and other materials processing. Certain deployments of residual stress are favorable, as they can greatly extend the fatigue life of a metal. However, in other deployments, the effect of residual stress can cause premature failure of a material.

Lindgren, Jones, Berger & Rosen, *Determining Residual Stress in Plates with Rayleigh Waves*, Conference on Progress in Quantitative Nondestructive Evaluation (Aug. 2–6, 1993), the disclosure of which is incorporated by reference, discloses the use of a tunable transducer to measure the amount of residual stress in an Inconel test sample at three different frequencies as the sample was elastically loaded in a three point bend test. From these measurements, velocity changes were detected with increasing elastic stress levels. By plotting the velocity changes as a function of increasing stress, the amount of residual stress present in the sample was detectable until the plastic limit of the material was reached. Similarly, Lindgren, Jones, Berger & Rosen, *Determining Residual Stress in Plates with Rayleigh Waves*, ASNT Spring Conference Summaries, p.52–54 (Mar. 20–24, 1995), the disclosure of which is incorporated by reference, discloses that changes in Rayleigh wave velocity are dependent on the state of stress in the material being tested.

Thus, Rayleigh wave velocity measurements are useful for mapping changes in material characteristics as a function of depth in a material: regardless of the nature of the generation and detection system, a depth profile of the material properties can be obtained. In addition, the similar measurements can be applied to evaluation and process control in other applications, such as measurement of chemical, microstructural and compositional changes in the near-surface region of a material, including coatings.

While this invention has been illustrated and described in accordance with a preferred embodiment, it is recognized that variations and changes may be made therein without departing from the invention as set forth in the claims.

What is claimed is:

1. A method for obtaining near-surface characteristics of a material, comprising the steps of:

generating, with a single generating system, a series of single frequency ultrasonic Rayleigh waves to provide a plurality of Rayleigh waves in the material;

detecting the Rayleigh waves with a detection system remote from the generating station;

determining velocities of the detected Rayleigh waves at the frequency generated by the generating equipment; and preparing a depth profile of one or more characteristics of the material based on the determined Rayleigh wave velocities.

2. The method as set forth in claim 1, wherein the detected Rayleigh wave is converted to digital signals.

3. The method as set forth in claim 2, comprising the further step of storing the digital signals in a storage device.

4. The method as set forth in claim 1, comprising the further steps of determining reference value of a velocity of a Rayleigh wave in a sample of the material, and comparing the reference value to the determined Rayleigh wave velocities.

5. The method as set forth in claim 1, wherein the Rayleigh waves are detected with a single detection system.

6. A system for determining near-surface characteristics of a material, comprising:

a single generator for generating a series of single frequency ultrasonic Rayleigh waves in the material;

a detection system, remote from the generator, for detecting the Rayleigh waves at the frequency generated by the generator;

processing means for calculating Rayleigh wave velocities based on a time of flight from generation of the Rayleigh waves by the generator to detection of the Rayleigh waves by the detection system and for preparing a depth profile of one or more characteristics of the material based on Rayleigh wave velocities.

7. The system as set forth in claim 6, wherein the generator, the detection system, and the processor are physically separate, modular components.

8. The system as set forth in claim 6, further comprising means for converting the detected Rayleigh wave to digital signals.

9. The system as set forth in claim 8, further comprising a storage device for storing the digital signals.

10. The system as set forth in claim 6, wherein the generator and the detection system are separated by a known distance, and the processing means measures elapsed times for each of the detected Rayleigh waves from generation of the Rayleigh waves by the generator until detection of the Rayleigh waves by the detection system, and divides the known distance by the elapsed times to determine velocities of the detected Rayleigh waves.

11. The system as set forth in claim 6, wherein the detection system includes a first detecting device and a second detecting device, the first and second detecting devices are separated from one another by a known distance, and the processing means measures elapsed times for each of the selected components of the detected Rayleigh waves from detection of the Rayleigh waves by the first detecting device until detection of the Rayleigh waves by the second detection device, and divides the known distance by the elapsed times.

12. The system as set forth in claim 6, wherein the Rayleigh waves are detected with a single detection system.

* * * * *

UNITED STATES PATENT AND TRADEMARK OFFICE
CERTIFICATE OF CORRECTION

PATENT NO. : 5,894,092
DATED : April 13, 1999
INVENTOR(S) : Eric A. LINDGREN et al.

It is certified that error appears in the above-identified patent and that said Letters Patent is hereby corrected as shown below:

Column 1, line 9, insert -- This invention was made with government support under contract NAS1-20583 awarded by NASA. The Government has certain rights in this invention--.

Signed and Sealed this

Fourteenth Day of September, 1999

*Attest:*

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,894,092
DATED : April 13, 1999
INVENTOR(S) : Lindgren et al.

It is certified that error appears in the above-identified patent and that said Letters Patent is hereby corrected as shown below:

Column 1,
Line 4, insert -- STATEMENT REGARDING FEDERALLY SPONSORED RESEARCH OR DEVELOPMENT   This invention was made with government support under contract NAS1-20583 awarded by NASA. The Government has certain rights in this invention. --

Signed and Sealed this

Fourteenth Day of January, 2003

JAMES E. ROGAN
*Director of the United States Patent and Trademark Office*